US012678039B2

(12) United States Patent
Sinha et al.

(10) Patent No.: US 12,678,039 B2
(45) Date of Patent: Jul. 14, 2026

(54) VISUAL FIELD TEST IN A VR HEADSET

(71) Applicant: Verily Life Sciences LLC, Dallas, TX (US)

(72) Inventors: Supriyo Sinha, Menlo Park, CA (US); Kirk Gossage, Pacifica, CA (US); Dimitri Azar, Chicago, IL (US)

(73) Assignee: Verily Health Inc., Dallas, TX (US)

( * ) Notice: Subject to any disclaimer, the term of this patent is extended or adjusted under 35 U.S.C. 154(b) by 357 days.

(21) Appl. No.: 18/537,645

(22) Filed: Dec. 12, 2023

(65) Prior Publication Data

US 2024/0197168 A1      Jun. 20, 2024

Related U.S. Application Data

(60) Provisional application No. 63/432,955, filed on Dec. 15, 2022.

(51) Int. Cl.
| | |
|---|---|
| *A61B 3/024* | (2006.01) |
| *A61B 3/00* | (2006.01) |
| *A61B 3/113* | (2006.01) |
| *G06F 3/01* | (2006.01) |

(52) U.S. Cl.
CPC .............. *A61B 3/024* (2013.01); *A61B 3/005* (2013.01); *A61B 3/113* (2013.01); *G06F 3/012* (2013.01)

(58) Field of Classification Search
CPC ......... A61B 3/024; A61B 3/005; A61B 3/113; A61B 3/0091; A61B 3/028; A61B 3/032; G06F 3/012; G06F 3/013
See application file for complete search history.

(56) References Cited

U.S. PATENT DOCUMENTS

| | | | |
|---|---|---|---|
| 9,301,675 B2 | 4/2016 | Kiderman et al. | |
| 10,231,614 B2 | 3/2019 | Krueger | |
| 10,288,910 B2 * | 5/2019 | Fayolle ................. | A61B 3/113 |
| 10,973,409 B2 * | 4/2021 | Kiderman ......... | G02B 27/0093 |
| 11,490,809 B2 | 11/2022 | Krueger | |
| 11,612,316 B2 | 3/2023 | Zidan et al. | |
| 11,857,258 B2 * | 1/2024 | Kiderman ......... | G02B 27/0093 |
| 12,178,509 B2 * | 12/2024 | Alvarez .............. | G02B 27/017 |
| 2017/0245753 A1 | 8/2017 | Donaldson | |
| 2017/0293356 A1 * | 10/2017 | Khaderi ................. | G06F 3/013 |
| 2017/0322430 A1 * | 11/2017 | Fayolle ............... | G02C 13/005 |
| 2019/0082954 A1 * | 3/2019 | Kiderman ............. | A61B 3/113 |

(Continued)

FOREIGN PATENT DOCUMENTS

| | | |
|---|---|---|
| JP | 59-12320 A | 1/1984 |
| JP | 2017-529964 A | 10/2017 |

(Continued)

OTHER PUBLICATIONS

International Search Report and Written Opinion received for PCT Patent Application No. PCT/US23/83897, mailed on May 27, 2024, 20 pages.

(Continued)

*Primary Examiner* — Navin Natnithithadha
(74) *Attorney, Agent, or Firm* — Christensen O'Connor Johnson Kindness PLLC

(57) ABSTRACT

Virtual reality, VR, headset-based electronic systems that can be used to perform visual field tests. The systems may improve the sensitivity, consistency, and case of application of the visual field test. Other aspects are also described.

19 Claims, 4 Drawing Sheets

(56) References Cited

U.S. PATENT DOCUMENTS

| | | | | |
|---|---|---|---|---|
| 2019/0150727 | A1 | 5/2019 | Blaha et al. | |
| 2020/0073143 | A1 | 3/2020 | Macnamara et al. | |
| 2020/0085298 | A1 | 3/2020 | Cornsweet et al. | |
| 2021/0275013 | A1 * | 9/2021 | Alvarez | G02B 27/017 |
| 2021/0345874 | A1 * | 11/2021 | Kiderman | G02B 27/0093 |

FOREIGN PATENT DOCUMENTS

| | | | | |
|---|---|---|---|---|
| JP | 2020-141848 | A | 9/2020 | |
| JP | 2021502881 | A | 2/2021 | |
| WO | WO-2017147141 | A1 * | 8/2017 | A61B 3/113 |
| WO | 2017182596 | A1 | 10/2017 | |
| WO | WO-2017177187 | A1 * | 10/2017 | A61B 3/10 |
| WO | WO-2019246098 | A1 * | 12/2019 | G02B 27/017 |

OTHER PUBLICATIONS

Jacob, Robert J.K., et al.; "Commentary on Section 4—Eye Tracking in Human-Computer Interaction and Usability Research: Ready to Deliver the Promises;" The Mind's Eye; Cognitive and Applied Aspects of Eye Movement Research; 2003; https://doi.org/10.1016/B978-044451020-4/50031-1; pp. 573-605.

"Active Eye Tracking+ Neighborhood Cluster Testing: A More Efficient Approach with a Positive Patient Experience;" Visual Field Testing: A Profound Transformation; M&S Technologies; MSTech-eyes.com; 8 pages.

Ramchandran, Rajeev S., et al.; "Visual Fields in Retinal Disease;" https://clinicalgate.com/visual-fields-in-retinal-disease-2/; Jun. 6, 2022; pp. 1-15.

Kim, Taehyung, et al.; "Experimental Verification of Objective Visual Fatigue Measurement Based on Accurate Pupil Detection of Infrared Eye Image and Multi-Feature Analysis;" Sensors 2020, 20, 4814; doi:10.3390/s20174814; www.mdpi.com/journal/sensors; Aug. 26, 2020; pp. 1-12.

Japanese Office Action mailed May 14, 2026, in corresponding Japanese Patent Application No. 2025-523852. Machine translation provided.

* cited by examiner

VISUAL FIELD TEST IN A VR HEADSET

CROSS-REFERENCE TO RELATED APPLICATIONS

This nonprovisional patent application claims the benefit of the earlier filing date of U.S. Provisional Application No. 63/432,955 filed 15 Dec. 2022.

FIELD

An aspect of the disclosure here relates to portable head worn equipment that can be used for performing visual field testing of the wearer's eyes.

BACKGROUND

Traditionally, visual field tests are performed using a resolute, bulky, and stationary (non-portable) computerized machine that is typically resting on a tabletop in a light-controlled room. The person whose vision is being tested sits in front of the machine and positions their head so that their eyes peer into a view port of the machine. An operator hands the person an electronic clicker (switch) and instructs the person to press a button of the clicker as soon as they can see a temporary light or object appearing in the view port. The machine electronically creates a static target that is visible in the view port, and the operator asks the person to fixate on the static target. The machine generates a sequence of the temporary lights or objects off to the side of the static target, at random locations with varying intensity, while the machine records the person's clicker responses. The machine then analyzes the relative timing between when each object in the sequence was generated and the person's clicks, while considering the location of that object, its intensity and perhaps whether or not the person remained fixated on the static target, to determine how well the person can see their visual field. If the test takes so long that the person gets tired of fixating on the target or maintaining their head against the viewer port then the results of the test could be unreliable.

SUMMARY

One aspect of the disclosure here is a virtual reality, VR, headset-based electronic system that can be used to perform a visual field test. These systems may improve the sensitivity, consistency, and ease of conducting the visual field test in various ambient light environments, in a more efficient (less time consuming) manner. The results of the visual field test may then be used by, for example, an eye care professional to diagnose a health problem with the person that might call for additional testing or a recommended treatment.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the Claims section. Such combinations may have advantages that are not recited in the above summary.

BRIEF DESCRIPTION OF THE DRAWINGS

Several aspects of the disclosure here are illustrated by way of example and not by way of limitation in the figures of the accompanying drawings in which like references indicate similar elements. It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

DETAILED DESCRIPTION

Several aspects of the disclosure with reference to the appended drawings are now explained. Whenever the shapes, relative positions and other aspects of the parts described are not explicitly defined, the scope of the invention is not limited only to the parts shown, which are meant merely for the purpose of illustration. Also, while numerous details are set forth, it is understood that some aspects of the disclosure may be practiced without these details. In other instances, well-known circuits, structures, and techniques have not been shown in detail so as not to obscure the understanding of this description.

Figure 1:
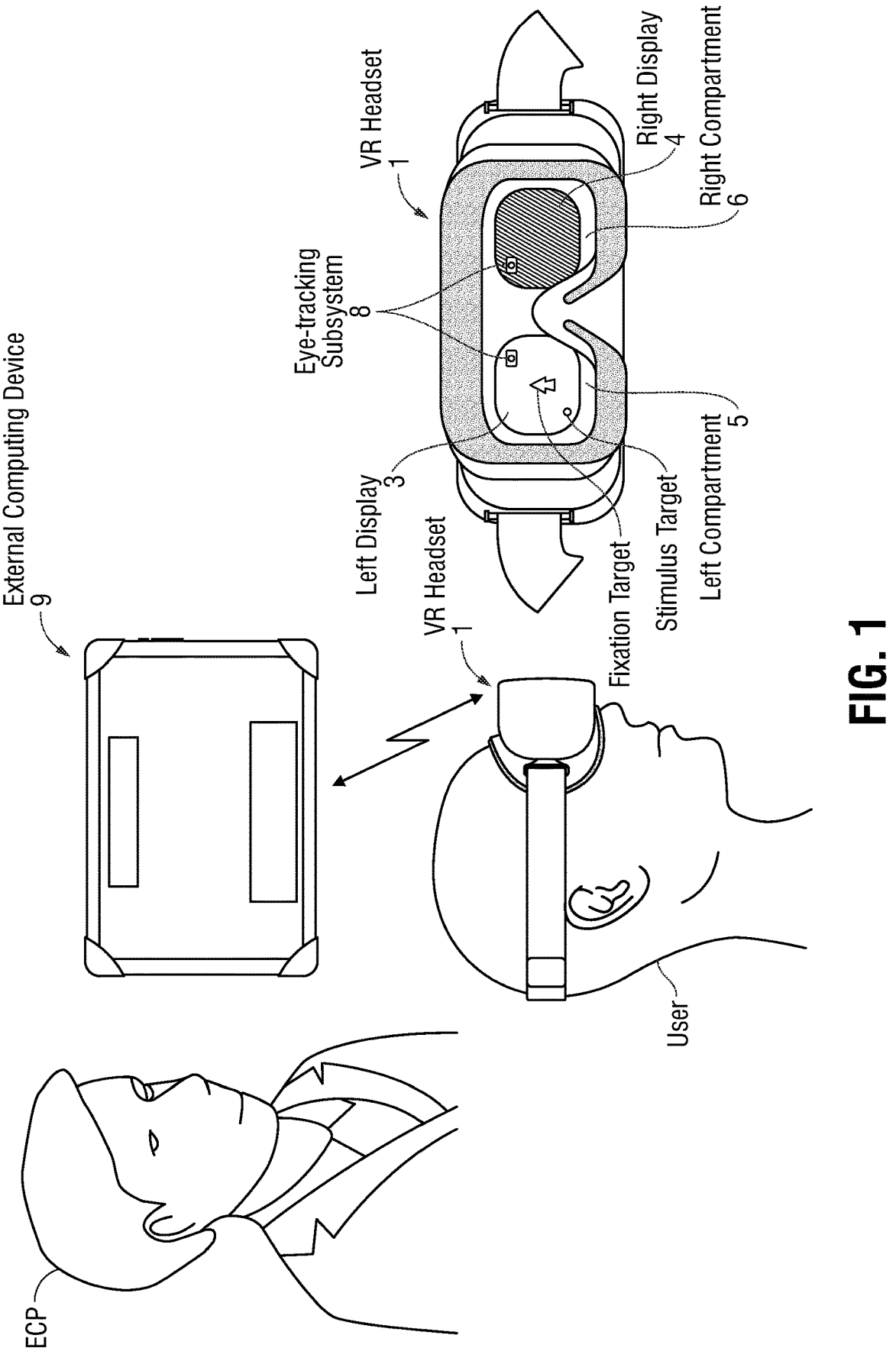
FIG. 1 is a diagram of an example virtual reality, VR, headset-based system for visual field testing.

FIG. 1 is a diagram of an example virtual reality, VR, headset-based system that can be used for visual field testing. The system is composed of a VR headset 1 which has a wired or wireless communication network interface for communicating data with an external computing device 9, e.g., a tablet computer, a laptop computer, etc. A human operator, such as an eye care professional, ECP, may interact briefly with software that is being executed by one or more microelectronic data processors (generically, "a processor") of the system to conduct the visual field test. Once launched or initialized the software may conduct the visual field test automatically (without input from the operator) by controlling the various electronic and optical components of the VR headset 1. The software may have components that are being executed by a processor that is in the VR headset 1, and it may have components that are executed by a processor which is part of the external computing device 9, while the VR headset 1 is fitted over the user's eyes as shown. Some of these software components may be executed either in the VR headset 1 or in the external computing device 9. The software may interact with the operator through a graphic user interface that uses a touchscreen of the external computing device 9, including presenting results of the visual field test.

The VR headset 1 may have a form factor like goggles, as shown, that blocks all ambient lighting outside of the VR headset 1 so as to create a light controlled environment around the user's eyes (that is independent of the ambient lighting outside of the VR headset 1). The VR headset 1 may be composed of a left visible light display 3 to which a left compartment 5 is coupled that fits over the left eye of the user, and a right visible light display 4 to which a right compartment 6 is coupled that fits over the right eye of the user. The left and right compartments are configured, e.g., shaped and being opaque, so that the user cannot see the right display 4 using only their left eye, and the user cannot see the left display 3 using only their right eye (once the VR headset 1 has been fitted over the user's eyes). Also, the left and right displays need not be separate display screens, as they could instead be the left and right halves of a single display screen. The displays may be implemented using technology that provides sufficient display resolution or pixel density, e.g., liquid crystal display technology, organic light emitting diode technology, etc. Although not shown, there may also be an eyecup over each of the left and right displays that includes optics (e.g., a lens) serving to give the user the illusion that an object they see in the display (in this example a pine tree, which may be displayed in 2D or in 3D) is at a greater distance than the actual distance from their eye to the display, thereby enabling more comfortable viewing. The VR headset 1 might also incorporate trial lenses or some other adjustable refractive optical system to accommodate patients with different refractive errors.

The VR headset 1 also has a non-visible light-based eye tracking subsystem 8, e.g., an infrared pupil tracking subsystem, whose output eye tracking data can be interpreted by the processor for independently tracking the positions of the left and right eyes, and for detecting blinks and pupil size or diameter of each eye, in a way that is invisible or transparent to the user.

The system has a processor that is configured by software, or instructions stored in a machine readable medium such as solid state memory, to conduct a visual field test, when the headset has been fitted over the user's eyes. The term "processor" here may refer to one or more microelectronic devices that are part of the external computing device 9, one or more that are within the housing of the VR headset 1, or a combination of microelectronic devices in the external computing device 9, the VR headset 1 and perhaps in another computing device that are communicating with each other through a digital communication interface. For example, the processor may be external to the VR headset 1 and receives through a wired or wireless communications network interface the tracking data from the eye tracking subsystem. The processor may be configured to signal a further display, for example the display screen of the external computing device 9, to display progress of or the results of visual field test.

The visual field test may proceed as follows, referring now to the operations depicted in the flow diagram of FIG. 2. Note here that unless clearly implied by context or explicitly mentioned, the operations of a method or process need not be performed sequentially in the order shown or described, as in some cases two or more operations can overlap in time or occur in a different order. Once the headset has been fitted over the user's eyes, the method begins in operation 11 with the processor signaling the left visible light display or the right visible light display to display a fixation target (a graphical object). In the example shown in the figure, the fixation target is a pine tree but more generally it can be any graphical object that serves as a fixation point at which the user may be asked to stare. Next, in operation 13, the processor signals the display to display a stimulus target, simultaneously with the fixation target. The stimulus target may be another graphical object, and it may or may not be the same graphical object each time operation 13 is performed, e.g., one time it is a horizontal line wiggling vertically, another time it might be a vertical line wiggling horizontally. Note that in most instances the left eye is tested separately from the right eye, in that the stimulus target is displayed by either the left display or the right display but not both simultaneously.

The processor in operation 14 also determines a stimulus angle of a stimulus vector. The stimulus vector may point from the fixation target to the stimulus target. The term "angle" is used here generically to refer to an angular value for example in degrees or a direction having a suitable level of granularity and may be relative to a reference axis such as a horizontal axis that originates or passes through a center of the fixation target. The stimulus angle represents the direction or angle at which the head of a user wearing the VR headset 1 is expected to move or orient itself, upon the user seeing the stimulus target being displayed in VR headset. In one aspect, the stimulus angle (of an associated stimulus target) may have been predetermined in a laboratory or factory by a system test or calibration procedure performed there (e.g., either for a reference system that uses another specimen or version of the VR headset 1, or for a production system that uses the actual VR headset 1). The predetermined stimulus angle would then be stored in memory of the production system, for example during initialization of the system. In another aspect, the stimulus angle may be determined by the production system "online" (or during the visual field test). This may be done, for example, by the processor determining the stimulus vector (e.g., as a vector drawn from the fixation target and whose tip represents the location of the stimulus target as displayed) and computing the angle of the stimulus vector relative to the reference axis.

In operation 16, the processor uses the tracking data from the eye tracking subsystem 8 to record a tracked position of the right eye or a tracked position of the left eye as the eye moves when the stimulus target appears due to operation 13. It also interprets the tracked position of the eye to determine a response angle of a response vector (operation 17). The response vector may be defined to point from the fixation target in the direction in which the eye has moved (due to the stimulus target appearing). The response angle may be computed as the angle of the response vector relative to the reference axis, e.g., where the processor computes the response vector and then determines the response angle by processing the response vector. The processor then records (operation 18) an indication as to whether the user has seen the stimulus target, based on performing a comparison between the stimulus angle and the response angle. For example, the processor computes a difference between the stimulus angle and the response angle, and when that difference is less than a threshold then the indication is that the user has seen the stimulus target. The processor repeats operations 11-18 several times each time with the stimulus target at a different location, to cover an entire field of view of the user and thereby complete a visual field test on the eye of the user. In this manner, the processor completes the visual field test on the user without receiving either manual or verbal input from the user on whether the user has seen the stimulus target each time.

In one aspect, the operations 11-18 are repeated on the same eye, each time with the stimulus target at a different location in the user's field of view, until there is sufficient coverage of the user's field of view as a result of which the visual field test has been completed for that eye. Those operations are then repeated on the other eye until the visual field test has been completed for that eye. In another aspect however, the visual field test is "interleaved" where in each pass the processor alternates the display of the stimulus target between the left eye and the right eye: the processor performs operations 11-18 one or more times on the left eye (with different stimulus target locations each time), and then repeats the operations 11-18 one or more times on the right eye (with different stimulus target locations each time), and then repeats operations 11-18 on the left eye, and then repeats them on the right eye, and so on until there is sufficient coverage of the field of views of both eyes at which point the visual field test of both eyes is complete. Note here that while displaying of the stimulus target alternates between the left display and the right display, the fixation target may remain displayed by both the left display and the right display. But in another variation, displaying of the fixation target follows the stimulus target, e.g., the fixation target appears in the left display and then the stimulus target also appears in the left display while the right display remains entirely dark or in a background color, and then the left display is signaled into the entirely dark or background color state while the fixation target appears in the right display followed with the stimulus target (and the fixation target disappears from the left display which then becomes entirely dark or in the background color).

In another aspect, the VR headset 1 also includes a head tracking subsystem that produces head tracking data. The head tracking data measures a tracked position or a tracked orientation of the head of the user. For example, the VR headset 1 may further include an accelerometer or a tilt sensor, and the processor is further configured to interpret output data of the accelerometer or the tilt sensor to determine a head response vector that points in a direction in which the user's head moves when the stimulus target appears. The indication (in operation 18) as to whether the user has seen the stimulus target in operation is now also based on a comparison (made by the processor) between the stimulus angle and an angle of the head response vector.

Figure 3:
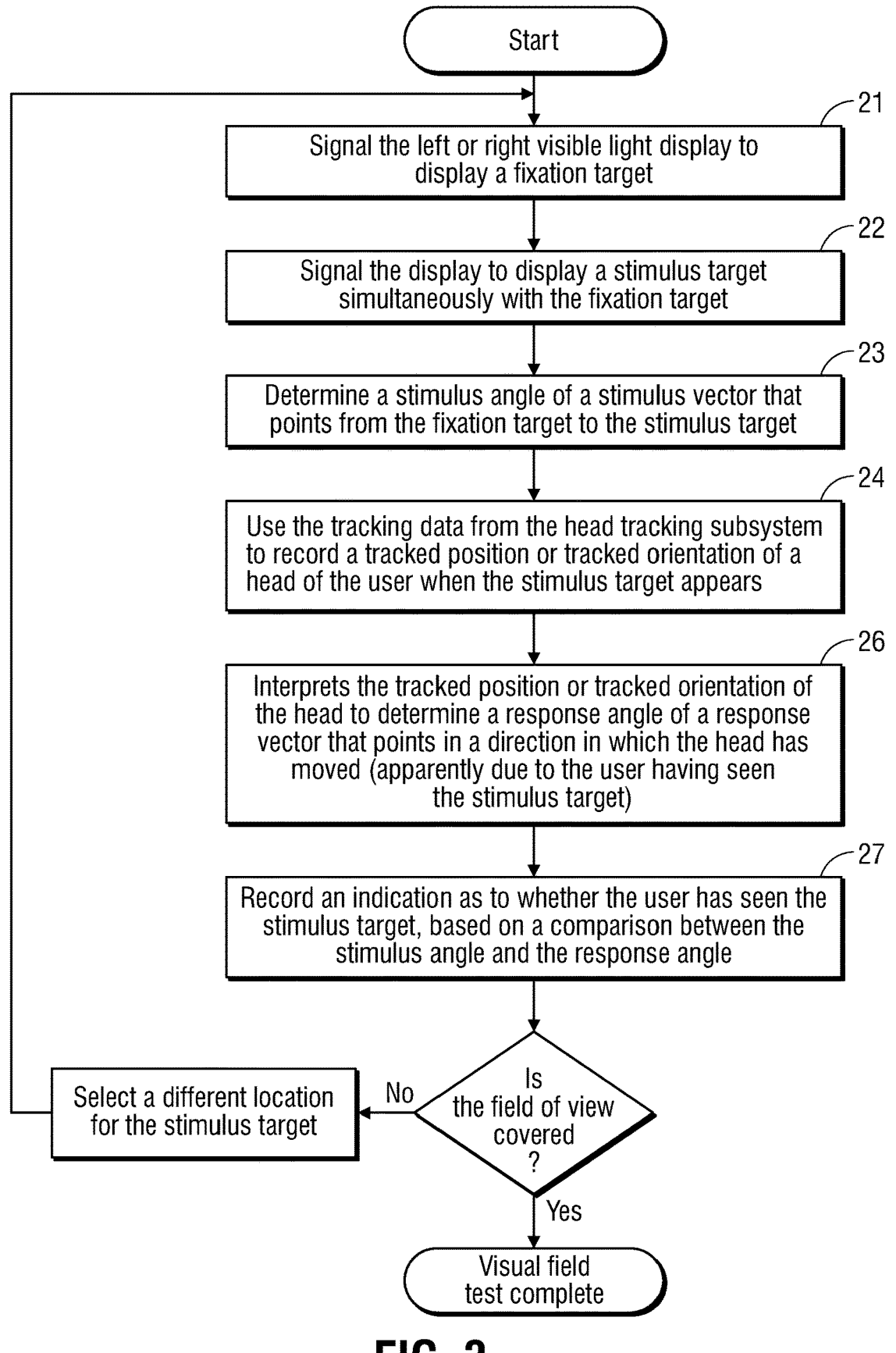
FIG. 3 is a flow diagram of another example visual field testing process performed by a VR headset based system that has a head tracking subsystem.

The head tracking data may also be used by itself, i.e., without using the eye tracking data, to perform a visual field test on the user, as illustrated in the example flow diagram of FIG. 3. There, the processor is configured to (when the headset has been fitted over the user's eyes) signal the left or right visible light display to display a fixation target (operation 21), and then a stimulus target simultaneously with the fixation target (operation 22). The processor determines a stimulus angle of a stimulus vector that points from the fixation target to the stimulus target (operation 23). It then uses the tracking data from the head tracking subsystem to record a tracked position or tracked orientation of a head of the user (operation 24) when the stimulus target appears due to operation 21. And in operation 26, the processor interprets the tracked position or tracked orientation of the head to determine a response angle of a response vector that points in a direction in which the head has moved (due to the user having seen the stimulus target). The processor then, in operation 27, records an indication as to whether the user has seen the stimulus target, based on a comparison between stimulus angle and the response angle.

Figure 2:
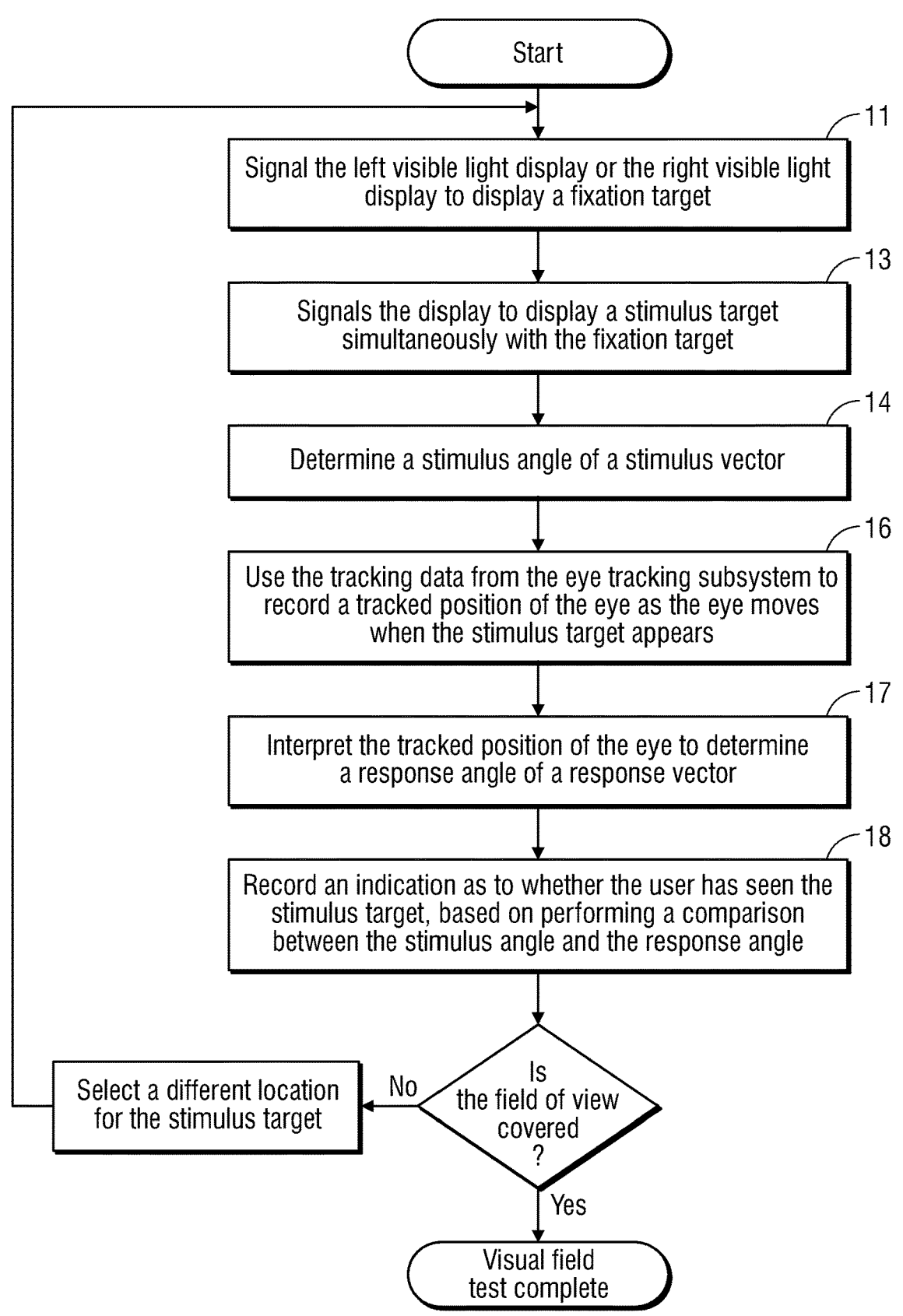
FIG. 2 is a flow diagram of an example visual field testing process performed by the system of FIG. 1.

Many of the aspects described above in connection with the eye tracking based method of FIG. 2 are also applicable to the head tracking based method of FIG. 3. For instance, the operations 21-27 may be repeated several times where each time the stimulus target appears at a different location in the user's field of view. In one aspect, the operations 21-27 are repeated in this manner until the visual field test has been completed for one eye, and then the operations are repeated to test the other eye. In another aspect, the processor alternates testing of the left eye and the right eye: the processor performs operations 21-27 one or more times on the left eye (with different stimulus target locations each time), and then repeats the operations 21-27 one or more times on the right eye (with different stimulus target locations each time), and then repeats operations 21-27 on the left eye, and so on, until testing of both eyes has been completed.

Some variations to the methods described above in connection with FIG. 2 and FIG. 3 are as follows. In one aspect, the processor compares not only the stimulus angle to the response angle (in operation 18 or in operation 27) but it also considers the magnitudes of the stimulus vector and the response vector, when determining whether the user has seen the stimulus target. As an example of such capability, the processor could determine the stimulus vector as defined by or having both the stimulus angle and a stimulus magnitude, and also determines the response vector as defined by or having both the response angle and a response magnitude. The indication as to whether the user has seen the stimulus target in this case is further based on the processor determining whether the response magnitude is i) greater than a noise threshold and ii) within a range of the stimulus magnitude. A more general statement on the latter criterium is that the processor is comparing the response magnitude with the stimulus magnitude. These two additional criteria for evaluating the excursion of the eye may result in greater accuracy for the test.

Also, the indication of whether or not the user has seen the stimulus target may be binary (i.e., correct, or incorrect), or it may instead have a confidence or probability associated with it, e.g., 80% confidence that the user saw the stimulus target.

In one variation, each time the processor repeats operations 11-18, or operations 21-27, the fixation target may remain stationary. In contrast, in another variation, the location of the fixation target changes (e.g., to that of the stimulus target when the last time the operations 11-18 were performed).

In yet another aspect, in operations 11-18 and in operations 21-27, the fixation target is displayed simultaneously by both the left display and by the right display (so that the fixation target is seen by both eyes simultaneously), while the stimulus target is displayed by only the left display or by only the right display (so that the stimulus target is seen by only one eye during the test).

In yet another variation, the VR headset 1 further includes a microphone, and the processor is further configured to interpret an output audio signal of the microphone to detect a vocal response (e.g., a particular word or a particular sound) when the stimulus target appears. In that case, the indication as to whether the user has seen the stimulus target (in operation 18 or operation 27) is further based on evaluating the vocal response. For example, the user may have been instructed to say the particular work or make the particular sound when they can see the stimulus target.

In yet another variation, the processor is configured in operation 13 or operation 22 to signal the left or right visible light displays to display the stimulus target as a moving target that starts to move inward. The stimulus target moves inward from a periphery of the user's field of view towards the fixation target. The operations 14-18 or operations 23-27 are performed on the moving stimulus target until the processor determines (in operation 28 or operation 27) that the user has seen the moving target. In one instance, the processor records an elapsed time from when the moving stimulus target started to move inward to when the processor determined that the user first sees the moving target. Based on knowledge of the velocity or speed of the moving target, and based on the elapsed time, the processor computes the position of the target when the user first sees the moving target, which position is representative of how far out the user can see in that direction. In another instance, the processor records the pixel position of the moving target when (the processor determines that) the user first sees the moving target, and that pixel position is representative of how far out the user can see in the direction of the moving target.

In the case where the stimulus target is stationary, it may be displayed in operation 13 or operation 22 as a stationary flash, e.g., 200 milliseconds in duration.

In another aspect, the processor may be configured to display the stationary stimulus target starting with a contrast or brightness that is insufficient to be seen by the user, and then increase the contrast or brightness until the processor determines (in operation 18 or operation 27) that the user can see the stimulus target, at which point the processor records a) an elapsed time from when the contrast or brightness started to increase until the user first sees the stimulus target or b) the contrast or brightness at which the user first sees the stimulus target. The contrast or brightness at which the user first sees the stimulus target is, along with the position or direction of the stimulus target, a data point for determining the extent to which the user can see in the direction of, or at the location of, the stationary stimulus target.

In yet another aspect, the processor, in operation 13 or in operation 22, is further configured to monitor the eye tracking data, the head tracking, or both, to detect when the user stops fixating on the fixation target. If the user has stopped fixating on the fixation target, then the processor waits, until the processor detects the user has resumed fixating on the fixation target, before signaling the left visible light display or the right visible light display to display the stimulus target. In another aspect, if the user has stopped fixating on the fixation target then the processor also signals the display to change the fixation target from a first color to a second color and then waits until it detects that the user has resumed fixating on the fixation target; and then at that point the processor signals the display to change the fixation target from the second color back to the first color. This gives useful feedback to the user.

In still another aspect, the VR headset 1 contains one or more light sensors that are used to detect levels of environmental light inside the left compartment and the right compartment. Although the VR headset 1 is designed to block all ambient light (outside of the headset), there may be some leakage. The processor is configured to record these levels of environmental light for the left compartment and the right compartment as representing external light contribution during the visual field test (while the user is wearing the VR headset).

In yet another aspect, the VR headset-based system of FIG. 1 may be used for visual field testing based on detecting blinks by the user. For example, consider the process depicted in FIG. 4 which is performed by the processor when the headset has been fitted over the user's eyes. Similar to what was described above in connection with FIG. 2 and FIG. 3, the processor is to signal the left visible light display or the right visible light display to display the fixation target (operation 31). In operation 34, the processor uses the tracking data from the eye tracking subsystem 8 to record a tracked position of the eye while the fixation target is being displayed, before the stimulus target appears. It interprets the tracked position of the eye to determine whether the user remains fixated on the fixation target (operation 35). If yes, then in operation 36 the processor signals the display to display a stimulus target simultaneously with the fixation. It then interprets the tracking data in operation 37 to detect a blink by the user when the stimulus target appears due to operation 36. The processor then records an indication as to whether the user has seen the stimulus target (operation 38), based on determining whether a duration of the blink is longer than a threshold, e.g., 0.5 seconds. The processor performs operations 31-38 several times, wherein each time the stimulus target is at a different location, to record a number of indications as to whether the user has seen the stimulus target at all of the distinct locations of the visual field test.

Figure 4:
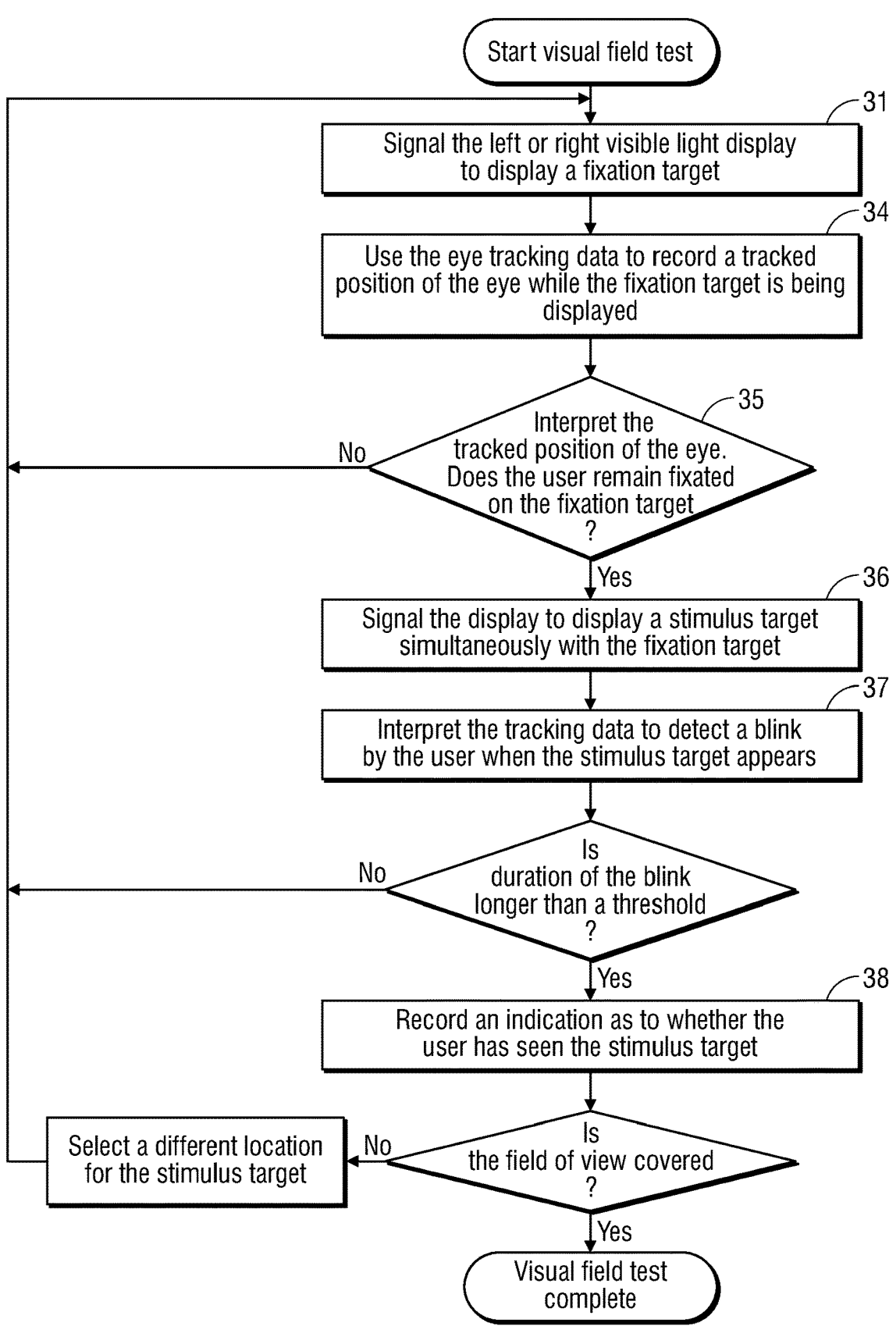
FIG. 4 is a flow diagram of another example visual field testing process performed by a VR headset based system that is based in part on blink detection.

Many of the aspects and variations described above in connection with the eye tracking based method of FIG. 2 and the head tracking based method of FIG. 3 are also applicable to the blink based method of FIG. 4. These include: the fixation target remaining stationary each time the processor performs operations 31-38, or a location of the fixation target may change in each pass; the visual field test being completed without receiving manual input from the user on whether the user has seen the stimulus target; the processor interpreting an output audio signal of a microphone to detect a vocal response when the stimulus target appears; the stimulus target being a moving target; the stimulus target being displayed as a stationary flash; the stimulus target being shown with increasing contrast or brightness until the processor determines that the user can see the stimulus target; waiting until the user resumed fixating on the fixation target before displaying the stimulus target; and changing color of the fixation target when the user stops fixating on it. Also, the blink based method of FIG. 4 may be combined with head tracking interpretations: the processor interprets output data of for example the accelerometer or the tilt sensor in the headset to determine a head response vector that points in a direction in which the user's head moves when the stimulus target appears due to operation 36, and the indication as to whether the user has seen the stimulus target in operation 38 is further based on the processing making a comparison between a stimulus angle of the stimulus vector (that is associated with the stimulus target) and an angle of the head response vector.

While certain aspects have been described and shown in the accompanying drawings, it is to be understood that such are merely illustrative of and not restrictive on the broad invention, and that the invention is not limited to the specific constructions and arrangements shown and described, since various other modifications may occur to those of ordinary skill in the art. For example, in the case where the VR headset 1 also has a head tracking subsystem, and the processor is external to the VR headset 1, the processor receives the head tracking data through a wired or wireless communications network interface from the head tracking subsystem. The description is thus to be regarded as illustrative instead of limiting.

What is claimed is:

1. A system adapted to perform visual field testing, the system comprising:
  a headset comprising:
    a left visible light display;
    a left compartment to fit over a left eye of a user;
    a right visible light display;
    a right compartment to fit over a right eye of the user, wherein the left and right compartments are configured so that when the headset has been fitted over the user's eyes i) the user cannot see the right visible light display using only their left eye and ii) the user cannot see the left visible light display using only their right eye, and a non-visible light-based eye tracking subsystem that produces tracking data for the left eye or for the right eye; and a processor configured to, when the headset has been placed to the user's eyes:

i) signal the left or right visible light display to display a fixation target, and then a stimulus target simultaneously with the fixation target;

ii) determine a stimulus angle of a stimulus vector that points from the fixation target to the stimulus target;

iii) use the tracking data from the eye tracking subsystem to record a tracked position of the right eye or a tracked position of the left eye as the right eye or the left eye moves when the stimulus target appears in i);

iv) interpret the tracked position of the right eye or the left eye to determine a response angle of a response vector that points in a direction in which the right eye or the left eye has moved;

v) record an indication as to whether the user has seen the stimulus target, based on a comparison between the stimulus angle and the response angle; and vi) map a visual field of the user based on the indication recorded for different locations of the stimulus target.

2. The system of claim 1 wherein the stimulus angle is predetermined in a laboratory or factory.

3. The system of claim 1 wherein the stimulus angle is computed by the processor online.

4. The system of claim 1 wherein the processor computes the stimulus vector and then determines the stimulus angle by processing the stimulus vector.

5. The system of claim 1 wherein the processor computes the response vector and then determines the response angle by processing the response vector.

6. The system of claim 1 wherein mapping the visual field of the user comprises the processor repeating i)-v) a plurality of times each time with the stimulus target at one of the different locations, to cover the visual field of the user for purposes of completing a visual field test on the left eye or the eye of the user.

7. The system of claim 6 wherein the processor completes the visual field test on the user without receiving manual or verbal input from the user on whether the user has seen the stimulus target each time.

8. The system of claim 6 wherein each time the processor performs i)-v), the fixation target remains stationary.

9. The system of claim 6 wherein each time the processor performs i)-v), a location of the fixation target changes.

10. The system of claim 1 wherein the indication is that the user has seen the stimulus target and is based on the processor computing a difference between the stimulus angle and the response angle which is less than a threshold.

11. The system of claim 1 wherein the processor determines the stimulus vector as defined by the stimulus angle and by a stimulus magnitude, and determines the response vector as defined by the response angle and a response magnitude, and the indication as to whether the user has seen the stimulus target is further based on the processor determining whether the response magnitude is i) greater than a noise threshold and ii) within a range of the stimulus magnitude.

12. The system of claim 1 wherein the processor determines the stimulus vector as defined by the stimulus angle and by a stimulus magnitude and determines the response vector as defined by the response angle and a response magnitude, and the indication as to whether the user has seen the stimulus target is further based on the processor comparing the response magnitude with the stimulus magnitude.

13. The system of claim 6 wherein the processor completes the visual field test on the user without receiving manual input from the user on whether the user has seen stimulus target at each of the plurality of distinct locations.

14. A system adapted to perform visual field testing, the system comprising:

a headset comprising:

a left visible light display;

a left compartment to fit over a left eye of a user;

a right visible light display;

a right compartment to fit over a right eye of the user, wherein the left and right compartments are configured so that when the headset has been fitted over the user's eyes i) the user cannot see the right visible light display using only their left eye and ii) the user cannot see the left visible light display using only their right eye, and a head tracking subsystem that produces tracking data; and a processor configured to, when the headset has been placed to the user's eyes:

i) signal the left or right visible light display to display a fixation target, and then a stimulus target simultaneously with the fixation target;

ii) determine a stimulus angle of a stimulus vector that points from the fixation target to the stimulus target;

iii) use the tracking data from the head tracking subsystem to record a tracked position or tracked orientation of a head of the user when the stimulus target appears in i);

iv) interpret the tracked position or tracked orientation of the head to determine a response angle of a response vector that points in a direction in which the head has moved;

v) record an indication as to whether the user has seen the stimulus target, based on a comparison between the stimulus angle and the response angle; and vi) map a visual field of the user based on the indication recorded for different locations of the stimulus target.

15. The system of claim 14 wherein the stimulus angle is predetermined in a laboratory or factory.

16. The system of claim 14 wherein the stimulus angle is computed by the processor online.

17. The system of claim 14 wherein the processor computes the stimulus vector and then determines the stimulus angle by processing the stimulus vector.

18. The system of claim 14 wherein the processor computes the response vector and then determines the response angle by processing the response vector.

19. A system comprising:

a headset comprising:

a left visible light display;

a left compartment to fit over a left eye of a user;

a right visible light display;

a right compartment to fit over a right eye of the user, wherein the left and right compartments are configured so that when the headset has been fitted over the user's eyes i) the user cannot see the right visible light display using only their left eye and ii) the user cannot see the left visible light display using only their right eye, and a non-visible light-based eye tracking subsystem that produces tracking data for the left eye or for the right eye; and a processor coupled to memory storing instructions that, when executed by the processor, cause the system to perform operations including:

i) signaling the left or right visible light display to display a fixation target, and then a stimulus target simultaneously with the fixation target;

ii) determining a stimulus angle of a stimulus vector that points from the fixation target to the stimulus target;

iii) using the tracking data from the eye tracking subsystem to record a tracked position of the right eye or a tracked position of the left eye as the right eye or the left eye moves when the stimulus target appears in i);

iv) interpreting the tracked position of the right eye or the left eye to determine a response angle of a response vector that points in a direction in which the right eye or the left eye has moved; and v) recording an indication as to whether the user has seen the stimulus target, based on a comparison between the stimulus angle and the response angle, wherein the indication is that the user has seen the stimulus target and is based on the processor computing a difference between the stimulus angle and the response angle which is less than a threshold.

* * * * *